US012252529B2

(12) United States Patent
Kim et al.

(10) Patent No.: US 12,252,529 B2
(45) Date of Patent: Mar. 18, 2025

(54) STREPTOCOCCUS PNEUMONIAE ANTISERUM WITHOUT CROSS-REACTIVITY AND METHOD FOR PRODUCING THE SAME

(71) Applicant: SK BIOSCIENCE CO., LTD., Seongnam-si (KR)

(72) Inventors: Hun Kim, Seongnam-si (KR); Yoon Jae Lee, Seongnam-si (KR); Seung-Beom Paik, Seongnam-si (KR); Jin-Hwan Shin, Seongnam-si (KR)

(73) Assignee: SK BIOSCIENCE CO., LTD., Gyeonggi-Do (KR)

( * ) Notice: Subject to any disclaimer, the term of this patent is extended or adjusted under 35 U.S.C. 154(b) by 737 days.

(21) Appl. No.: 17/429,089

(22) PCT Filed: Feb. 6, 2020

(86) PCT No.: PCT/KR2020/001707
§ 371 (c)(1),
(2) Date: Aug. 6, 2021

(87) PCT Pub. No.: WO2020/162689
PCT Pub. Date: Aug. 13, 2020

(65) Prior Publication Data
US 2022/0127339 A1 Apr. 28, 2022

(30) Foreign Application Priority Data
Feb. 7, 2019 (KR) .................. 10-2019-0014539

(51) Int. Cl.
*C07K 16/12* (2006.01)
*A61P 31/04* (2006.01)
*C07K 16/06* (2006.01)
*G01N 33/569* (2006.01)

(52) U.S. Cl.
CPC .......... *C07K 16/1275* (2013.01); *A61P 31/04* (2018.01); *C07K 16/06* (2013.01); *G01N 33/56944* (2013.01); *C07K 2317/10* (2013.01); *C07K 2317/33* (2013.01); *C07K 2317/35* (2013.01)

(58) Field of Classification Search
None
See application file for complete search history.

(56) References Cited

U.S. PATENT DOCUMENTS

| 10,259,865 | B2 * | 4/2019 | Mond | ..................... A61K 35/16 |
| 2002/0110562 | A1 * | 8/2002 | Adamou | ............ C07K 16/1275 424/190.1 |
| 2005/0106130 | A1 | 5/2005 | Lawman | |
| 2013/0195876 | A1 * | 8/2013 | Smith | ............... G01N 33/56944 424/139.1 |
| 2017/0102385 | A1 | 4/2017 | Ochs-Onolemhemhen et al. | |
| 2018/0117136 | A1 | 5/2018 | Babb et al. | |

FOREIGN PATENT DOCUMENTS

| WO | 2011-027364 A2 | 3/2011 | |
| WO | WO-2013115962 A2 * | 8/2013 | .............. A61P 31/04 |

OTHER PUBLICATIONS

Chi-Jen Lee, Journal of Biological Standardization vol. 11, issue 1, 1983 (Year: 1983).*
International Search Report for International Application No. PCT/KR2020/001707, dated Jun. 19, 2020.
Whitney CG et al., Decline in Invasive Pneumococcal Disease after the Introduction of Protein-Polysaccharide Conjugate Vaccine, N Engl J Med, 348(18):1737-46, 2003.
Crain et al., "Pneumococcal Surface Protein A (PspA) is Serologically Highly Variable and is Expressed by All Clinically Important Capsular Serotypes of *Streptococcus pneumoniae*", *Infection and Immunity* 58(10):3293-3299 (1990).
Darrieux et al., "Recognition of pneumococcal isolates by antisera raised against PspA fragments from different clades", *Journal of Medical Microbiology* 57:273-278 (2008).
Extended European Search Report for European Application No. 20752212.9, dated Oct. 4, 2022, 7 pages.
Gertz et al., "Nonpneumococcal Strains Recently Recovered from Carriage Specimens and Expressing Capsular Serotypes Highly Related or Identical to Pneumococcal Serotypes 2, 4, 9A, 13, and 23 A", *American Society for Microbiology* 12(3):e01037-21 (2021).

* cited by examiner

*Primary Examiner* — Jana A Hines
*Assistant Examiner* — Khatol S Shahnan Shah
(74) *Attorney, Agent, or Firm* — Lathrop GPM LLP; Brian C. Trinque

(57) ABSTRACT

The present invention relates to a *Streptococcus pneumoniae* antiserum without cross-reactivity and method for producing the same, more specifically, it relates to a method for producing a *S. pneumoniae* antiserum comprising the step of removing cross-reactivity using *S. pneumoniae* and a *S. pneumoniae* antiserum prepared by the method. The *Streptococcus pneumoniae* antiserum prepared according to the method of the present invention has very high specificity for a particular serotype, since the cross-reactivity with *S. pneumoniae* of serotypes expressing capsular polysaccharides of similar structure is removed. Therefore, it can be very useful in the related art that requires accurate quantification of *S. pneumoniae* capsular polysaccharide.

12 Claims, No Drawings

STREPTOCOCCUS PNEUMONIAE ANTISERUM WITHOUT CROSS-REACTIVITY AND METHOD FOR PRODUCING THE SAME

CROSS REFERENCE TO RELATED APPLICATION

This application is a 35 U.S.C. § 371 filing of International Patent Application No. PCT/KR2020/001707, filed Feb. 6, 2020, which claims priority to Korean Patent Application No. 10-2019-0014539, filed Feb. 7, 2019, which is incorporated herein by reference in its entirety.

TECHNICAL FIELD

The present application claims priority from and the benefit of Korean Patent Application No. 10-2019-0014539 filed on Feb. 7, 2019, which is hereby incorporated by reference for all purposes as if fully set forth herein.

The present invention relates to a *Streptococcus pneumoniae* antiserum without cross-reactivity and method for producing the same, more specifically, it relates to a method for producing a *S. pneumoniae* antiserum comprising the step of removing cross-reactivity using *S. pneumoniae* and the *S. pneumoniae* antiserum prepared by the method.

BACKGROUND ART the family of *Lactobacillus* streptococci and causes diseases such as pneumonia, meningitis, sepsis, and otitis media in humans. *S. pneumoniae* have a capsule, a polysaccharide coating that surrounds each cell, and the polysaccharides in the capsule act as antigens inducing the production of antibodies in the human body. In addition, *S. pneumoniae* are classified into about 90 or more serotypes according to the serological characteristics of capsular polysaccharides (capsular PS). Of these, 37 serotypes have been identified to cause serious invasive diseases. Anyone can get this *S. pneumoniae* disease, but in particular, children under 2 years of age and elderly people of 65 years or older are known to be vulnerable to *S. pneumoniae* infection.

Antibiotics are used for the treatment of *S. pneumoniae* disease, and vancomycin, levofloxacin, or moxifloxacin, which are not resistant to *S. pneumoniae*, are usually prescribed. *S. pneumoniae* infectious diseases can be treated only by antibiotic treatment and rest if healthy people, but it can be fatal to infants and elderly people with weak immunity, it is important to prevent by vaccination.

In order to prevent *S. pneumoniae* diseases, polysaccharide vaccines or polysaccharide-conjugate vaccines have been prepared and used using *S. pneumoniae* capsular polysaccharides. Polysaccharide vaccines have been proven to be effective in preventing *S. pneumoniae* disease in elderly and high-risk patients, but polysaccharide vaccines have not been proven effective in infants and children. In contrast, polysaccharide-conjugate vaccines have been demonstrated to be highly immunogenic and effective against invasive diseases and otitis media in infants and children (Whitney C G et al., *N Engl J Med*, 348 (18): 1737-46, 2003).

Recently, in order to increase the invasive disease prevention effect of *S. pneumoniae* polysaccharide-conjugate vaccine, development has been made in the direction of increasing the type and content of capsular polysaccharides. Therefore, accurate quantitative analysis is important, and appropriate methods are particularly important as the capsular polysaccharides added are diversified.

Immunochemical assays are biochemical test that measures the concentration of antigen or antibody through the antigen-antibody reaction. Compared with chemical analysis, it has high specificity and is used for diagnosis, analysis of clinical samples, and quality control of biological products. There are various types of immunochemical assays, such as enzyme-linked immunosorbent assay, radioimmunoassay and rate nephelometry, and there are some differences in the principles depending on the methods.

Since these assays utilize specific reactions between antigens and antibodies, they have been used for the quality control of multivalent vaccines comprising various antigens, such as *S. pneumoniae* polysaccharide vaccines, *S. pneumoniae* conjugate vaccines, or meningococcal conjugate vaccines. The content of antigens (capsular polysaccharide) of each serotype contained in the *S. pneumoniae* conjugate vaccine can be measured by obtaining a quantitative curve using the serotype-specific antiserum, thereby determining whether the antigen contents meet the Criteria of finished products. However, for serotypes with very similar antigenic structures, a problem arises in that the accuracy is reduced due to the cross-reactivity of antiserum. For example, *S. pneumoniae* serotypes 6A and 6B capsular polysaccharides comprise the same type of monosaccharides, and their structures are very similar. Therefore, serotype 6A antiserum not only reacts with serotype 6A capsular polysaccharide, but also cross-reacts with serotype 6B capsular polysaccharide. Such cross-reactivity of antiserum is one of the factors that hinder the accuracy of antigen quantitation, which leads to a decrease in vaccine efficacy. Recently, *S. pneumoniae* conjugate vaccines have been developed in the direction of increasing serotypes contained in order to increase the effect of preventing invasive *S. pneumoniae* disease, thereby increasing the possibility of antiserum cross-reactivity. There are existing commercially available *S. pneumoniae* antisera, but depending on the serotype, it may be cross-reactive. Therefore, in order to increase the accuracy of antigen quantitation, the preparation of antigen-specific antiserum without cross-reactivity is essential.

Non-patent article: Whitney C G et al., N Engl J Med, 348(18):1737-46, 2003

DISCLOSURE OF INVENTION

Technical Problem

Accordingly, the present inventors have repeatedly studied to produce *S. pneumoniae* antiserum that does not cross-react with other serotypes of *S. pneumoniae* and shows very high specificity with *S. pneumoniae* of specific serotypes of interest. As a result, the present inventor discovered that *S. pneumoniae* antiserum that is highly specific to particular *S. pneumoniae* can be prepared by removing the cross-reactivity using *S. pneumoniae* of different serotypes from the serotypes of *S. pneumoniae* used in the preparation of antiserum, thereby completing the present invention.

Therefore, an aspect of the present invention is to provide a method for preparing antiserum of *Streptococcus pneumoniae*, the method comprising the steps of:

(a) administering *Streptococcus pneumoniae* to a subject;
(b) collecting a serum from the subject;
(c) mixing the collected serum with *Streptococcus pneumoniae* of different serotype from the *Streptococcus pneumoniae* in the step (a) and confirming the presence or absence of cross-reactivity; and (d) removing an aggregated complex induced by cross-reactivity, in case where the presence of cross-reactivity is confirmed in the step (c).

Another aspect of the present invention is to provide an antiserum of *Streptococcus pneumoniae* prepared according to the method above.

Still, another aspect of the present invention is to provide a pharmaceutical composition for preventing or treating infectious diseases caused by *Streptococcus pneumoniae*, the composition comprising the antiserum as an active ingredient.

Still, another aspect of the present invention is to provide a pharmaceutical composition for preventing or treating infectious diseases caused by *Streptococcus pneumoniae*, the composition (essentially) consisting of the antiserum as an active ingredient.

Still, another aspect of the present invention is to provide a composition for diagnosing infectious diseases caused by *Streptococcus pneumoniae*, the composition comprising the antiserum.

Still, another aspect of the present invention is to provide a composition for diagnosing infectious diseases caused by *Streptococcus pneumoniae*, the composition (essentially) consisting of the antiserum.

Still, another aspect of the present invention is to provide a composition for quantifying antigens of *Streptococcus pneumoniae*, the composition comprising the antiserum.

Still, another aspect of the present invention is to provide a composition for quantifying antigens of *Streptococcus pneumoniae*, the composition (essentially) consisting of the antiserum.

Still, another aspect of the present invention is to provide a method for quantifying antigens of *Streptococcus pneumoniae*, the method comprising the steps of:

(a) reacting standard samples with the *Streptococcus pneumoniae* antiserum, wherein the antigen amount of the standard samples is specified;

(b) analyzing the turbidity of the standard samples resulting from the reaction of step (a) and obtaining a standard curve;

(c) reacting a sample to be detected with the *Streptococcus pneumoniae* antiserum; and (d) analyzing the turbidity of the sample resulting from the reaction in the step (c) and calculating the quantity of the antigens by applying the turbidity to the standard curve.

Still, another aspect of the present invention is to provide use of the antiserum of *Streptococcus pneumoniae* for preparing an agent for preventing or treating infectious diseases caused by *Streptococcus pneumoniae*.

Still, another aspect of the present invention is to provide a method for treating infectious diseases caused by *Streptococcus pneumoniae* in a subject, the method comprising administering an effective amount of a composition comprising, as an active ingredient, the antiserum of *Streptococcus pneumoniae* to the subject in need thereof.

Still, another aspect of the present invention is to provide use of the antiserum of *Streptococcus pneumoniae* for preparing an agent for diagnosing infectious diseases caused by *Streptococcus pneumoniae*.

Still, another aspect of the present invention is to provide use of the antiserum of *Streptococcus pneumoniae* for preparing an agent for quantifying antigens of *Streptococcus pneumoniae*.

Solution to Problem

Accordingly, in accordance with an aspect of the present invention, there is provided a method for preparing antiserum of *Streptococcus pneumoniae*, the method comprising the steps of:

(a) administering *Streptococcus pneumoniae* to a subject;

(b) collecting a serum from the subject;

(c) mixing the collected serum with *Streptococcus pneumoniae* of different serotype from the *Streptococcus pneumoniae* in the step (a) and confirming the presence or absence of cross-reactivity; and (d) removing an aggregated complex induced by cross-reactivity, in case where the presence of cross-reactivity is confirmed in the step (c).

In accordance with another aspect of the present invention, there is provided an antiserum of *Streptococcus pneumoniae* prepared according to the method above.

In accordance with another aspect of the present invention, there is provided a pharmaceutical composition for preventing or treating infectious diseases caused by *Streptococcus pneumoniae*, the composition comprising the antiserum as an active ingredient.

In accordance with another aspect of the present invention, there is provided a pharmaceutical composition for preventing or treating infectious diseases caused by *Streptococcus pneumoniae*, the composition (essentially) consisting of the antiserum as an active ingredient.

In accordance with another aspect of the present invention, there is provided a composition for diagnosing infectious diseases caused by *Streptococcus pneumoniae*, the composition comprising the antiserum.

In accordance with another aspect of the present invention, there is provided a composition for diagnosing infectious diseases caused by *Streptococcus pneumoniae*, the composition (essentially) consisting of the antiserum.

In accordance with another aspect of the present invention, there is provided a composition for quantifying antigens of *Streptococcus pneumoniae*, the composition comprising the antiserum.

In accordance with another aspect of the present invention, there is provided a composition for quantifying antigens of *Streptococcus pneumoniae*, the composition (essentially) consisting of the antiserum.

In accordance with another aspect of the present invention, there is provided a method for quantifying antigens of *Streptococcus pneumoniae*, the method comprising the steps of:

(a) reacting standard samples with the *Streptococcus pneumoniae* antiserum, wherein the antigen amount of the standard samples is specified;

(b) analyzing the turbidity of the standard samples resulting from the reaction of step (a) and obtaining a standard curve;

(c) reacting a sample to be detected with the *Streptococcus pneumoniae* antiserum; and (d) analyzing the turbidity of the sample resulting from the reaction in the step (c) and calculating the quantity of the antigens by applying the turbidity to the standard curve.

In accordance with another aspect of the present invention, there is provided use of the antiserum of *Streptococcus pneumoniae* for preparing an agent for preventing or treating infectious diseases caused by *Streptococcus pneumoniae*.

In accordance with another aspect of the present invention, there is provided a method for treating infectious diseases caused by *Streptococcus pneumoniae* in a subject, the method comprising administering an effective amount of a composition comprising, as an active ingredient, the antiserum of *Streptococcus pneumoniae* to the subject in need thereof.

In accordance with another aspect of the present invention, there is provided use of the antiserum of *Streptococcus pneumoniae* for preparing an agent for diagnosing infectious diseases caused by *Streptococcus pneumoniae*.

In accordance with another aspect of the present invention, there is provided use of the antiserum of *Streptococcus pneumoniae* for preparing an agent for quantifying antigens of *Streptococcus pneumoniae*.

Hereinafter, the present invention will be described in detail.

The present invention provides a method for preparing antiserum of *Streptococcus pneumoniae*, the method comprising the steps of:

(a) administering *Streptococcus pneumoniae* to a subject;
(b) collecting a serum from the subject;
(c) mixing the collected serum with *Streptococcus pneumoniae* of different serotype from the *Streptococcus pneumoniae* in the step (a) and confirming the presence or absence of cross-reactivity; and
(d) removing an aggregated complex induced by cross-reactivity, in case where the presence of cross-reactivity is confirmed in the step (c).

As used herein, the term "antiserum", also called immune serum, means a serum containing antibodies. Antiserum includes antibodies in the form of a mixture of IgG, IgM, IgA, IgE, and IgD immunoglobulins and many other serum proteins. In this case, when the antibodies are contained in the serum, it is relatively stable when kept at a low temperature, but when other serum proteins are removed by purification, these are easy to cause degeneration. Therefore, in the present invention, the antiserum may be one in which serum proteins other than antibodies are not removed, but the present invention is not limited thereto, and the method of the present invention can be equally applicable to the preparation of monoclonal or polyclonal antibodies in purified form.

Meanwhile, as described above, *S. pneumoniae* have been found to have about 90 or more serotypes so far depending on their serological characteristics, and the capsular polysaccharides of *S. pneumoniae* differ slightly depending on the serotypes. However, even though the serotypes of *S. pneumoniae* are different, there are *S. pneumoniae* comprising the same types of monosaccharides that make up capsular polysaccharides, and the structure of capsular polysaccharides of which are very similar. Therefore, even if it is made with antiserum against a particular serotype, it can react with *S. pneumoniae* capsular polysaccharides of other serotypes. As such, the reaction with *S. pneumoniae* capsular polysaccharides of other serotypes than the desired serotypes of *S. pneumoniae* are called cross-reactivity, and antiserum that has not been completely removed cross-reactivity is significantly lower in its usefulness. It is also the cause of lowering the reliability of analysis results using the antiserum.

The method for preparing antiserum of *S. pneumoniae* according to the present invention relates to a method for preparing antiserum having a very high specificity to the *S. pneumoniae* of the desired serotype by thoroughly removing cross-reactivity.

Each step of the method for preparing antiserum of the present invention will be described in more detail below.

(a) Administering *Streptococcus pneumoniae* to a Subject;

The step (a) is a step of inducing an immune response by administering to a subject *S. pneumoniae* (pneumococci) of a serotype to which antiserum is to be obtained, thereby inducing an antibody production against the administered *S. pneumoniae* in the blood of the subject.

As used herein, the term "*Streptococcus pneumoniae* (pneumococci)" refers to gram-positive bacteria belonging to the *Lactobacillus Streptococcus* family. *S. pneumoniae* are classified into about 90 or more serotypes according to the serological characteristics of capsular polysaccharides (capsular PS). In the present invention, the *S. pneumoniae* are selected from *S. pneumoniae* of all serotypes known to the art, and *S. pneumoniae* of all serotypes that will be newly revealed in the future.

Preferably, the *S. pneumoniae* can be selected from the group consisting of serotypes 1, 2, 3, 4, 5, 6A, 6B, 7F, 8, 9N, 9V, 10A, 11A, 12F, 13, 14, 15B, 17F, 18C, 19A, 19F, 20, 22F, 23F and 33F, and more preferably, the *S. pneumoniae* can be selected from the group consisting of serotypes 1, 3, 4, 5, 6A, 6B, 7F, 8, 9N, 9V, 10A, 11A, 12F, 14, 15B, 18C, 19A, 19F, 22F, 23F and 33F.

In the present invention, the *S. pneumoniae* can be live *S. pneumoniae*, inactivated *S. pneumoniae* or live attenuated *S. pneumoniae*, preferably, inactivated *S. pneumoniae* or live attenuated *S. pneumoniae*, most preferably, inactivated *S. pneumoniae*.

The term "inactivated *S. pneumoniae*" in the present invention means the same as dead *S. pneumoniae*, and various physical and chemical methods of inactivation are known in the art. More specifically, "inactivated *S. pneumoniae*" is inactivated *S. pneumoniae* having immunogenicity, and can be induced by irradiation (ultraviolet (UV), X-ray radiation, electron beam or gamma radiation), heating, chemical treatment, and the like.

In one embodiment, the *S. pneumoniae* can be inactivated by treatment of an inactivating agent. Suitable inactivating agents include beta-propiolactone, binary or beta- or acetylethyleneimine, glutaraldehyde, ozone, formalin (formaldehyde), and the like.

The term "live attenuated" in the present invention means to reduce the toxicity of the *S. pneumoniae*. In the present invention, "live attenuated" is synonymous with "nontoxic". In the present invention, the live attenuated *S. pneumoniae* are bacteria that have reduced toxicity and do not cause clinical signs, but can induce an immune response in the subject and the live attenuated *S. pneumoniae* can be obtained by attenuating methods common in the art. The live attenuated *S. pneumoniae* that have lost or attenuated pathogenicity can be prepared by, for example, irradiating, heating, treating chemicals causing attenuation, deleting or damaging single or multiple genes using bacteriophages, leukocytes or genetic engineering techniques.

In the step (a) of the present invention, *S. pneumoniae* administered to the subject induce a humoral immune response, and as a result can produce antibodies in the subject. In the art, a method of inducing an immune response by inoculating bacteria to a subject is well known, and these known methods can be applied to the present invention as it is.

In the present invention, the subject is not particularly limited in kind but is preferably a mammal or a bird. The mammal can be a mouse, rat, rabbit, goat, guinea pig, cow, horse, dog, cat, goat, sheep or pig, and the bird may be chicken, duck or turkey.

(b) Collecting a Serum from the Subject;

In the method of the present invention, the step (b) is a step of separating serum after collecting blood from the subject in which the immune response is induced by the step (a).

As used herein, the term "serum" refers to the part of blood in which fibrinogen is removed from plasma from which cellular components (red blood cells, white blood cells, platelets) are removed among blood components. The serum comprises various proteins (albumin, globulin, fibronectin, fetuin, α2-macroglobulin, transferrin, etc.), hormones, inorganic substances, nutrients, metabolites, as well as antibodies produced by inoculation of S. pneumoniae. In particular, the present invention does not induce an immune response in the subject by administering purified antigens, but induces an immune response by administering S. pneumoniae of a specific serotype to the subject. Therefore, polyclonal antibodies against S. pneumoniae administered are contained in the serum.

The time point of obtaining the blood after administering S. pneumoniae to the subject in the step (a) may vary depending on the state of the administered S. pneumoniae, experimental conditions, the type of animal, and the degree of immune response of the subject. The time of blood collection can be determined by measuring an antibody titer in the blood obtained from the subject. If the antibody titer is too low, an additional inoculation with S. pneumoniae can be performed to boost the immune response. Preferably, if the antibody titer is analyzed by nephelometry by diluting the serum obtained from the subject by six times, the serum can be separated from the blood at the time point when the response value (Rate unit) is 20 or more against an antigen amount of 1 ug/mL, and is 150 or more against an antigen amount of 6 ug/mL.

In the present invention, the nephelometry is a method of measuring scattering of light due to immunoprecipitation caused by the reaction between antigens and antibodies (sample), and it is a method of measuring the rate of change of scattered light over time using a rate unit as unit. In the nephelometry, the antigen-antibody reaction is performed in cells through which light passes, and the light passing through is scattered due to the antigen-antibody complex formed by precipitation. Since the intensity of the scattered light changes in proportion to the amount of the generated antigen-antibody complex, it is possible to obtain a quantitative curve for the amount of antigen by keeping the amount of antibody constant and changing the amount of antigen. On the contrary, if the amount of the antigen is kept constant and the amount of the antibody is changed, a quantitative curve for the amount of the antibody can be obtained.

As used herein, the term "antibody titer" refers to the inverse number of the dilution factor of antiserum when the response to the S. pneumoniae standard solution satisfies criteria. In one embodiment of the present invention, the antibody titer of the antiserum at the appropriate parameter condition of nephelometer is defined as the inverse number of the dilution factor of antiserum when the response value (Rate unit) satisfies the criteria against standard solution of 1.0 ug/mL and 6.0 ug/mL, that is the response value is 20 or more against an antigen amount of 1 ug/mL, and is 150 or more against an antigen amount of 6 ug/mL. The antibody titer of antiserum for preparation can be defined as the inverse number of the dilution factor of antiserum, the response value of which against standard solution of 1.0 ug/mL and 6.0 ug/mL at the appropriate parameter condition of nephelometer satisfies the criteria, and the coefficient of determination ($R^2$) of quantitative curve of which is 0.98 or more.

As used herein, the term "standard solution" refers to a series of standard solutions obtained by diluting a standard substance having a known concentration with a buffer so that the capsular polysaccharide derived from S. pneumoniae of a particular serotype has a predetermined concentration. For example, the series of standard solutions may be 1.0 μg/ml to 10.0 μg/ml, such as 1.0 μg/ml, 2.0 μg/ml, 3.0 μg/ml, 4.0 μg/ml, 5.0 μg/ml, 6.0 μg/ml, 7.0 μg/ml, 8.0 μg/ml, 9.0 μg/ml, and 10.0 μg/ml of the capsular polysaccharide concentration range. Theoretical standard solution concentrations can be determined through calibration curve by plotting against the measured mean response values of the repeated set of concentrations of each standard solution, and calculating the slope, y-intercept and the coefficient of determination ($R^2$) by linear regression analysis.

(c) Mixing the Collected Serum with Streptococcus pneumoniae of Different Serotype from the Streptococcus pneumoniae in the Step (a) and Confirming the Presence or Absence of Cross-Reactivity;

In the method of the present invention, the step (c) is a step of confirming whether cross-reactivity occurs by inducing aggregation reaction of antigen-antibody reaction by mixing the serum obtained in the step (b) with S. pneumoniae of different serotypes from S. pneumoniae in the step (a)

The "S. pneumoniae of different serotypes from S. pneumoniae in the step (a)" can be S. pneumoniae of any serotypes except for the S. pneumoniae of serotypes administered to the subject in the step (a) to produce antiserum.

As an example, when preparing antiserum against serotype 10A S. pneumoniae using the method of the present invention, the "S. pneumoniae of different serotypes from S. pneumoniae in the step (a)" can be all serotypes except for serotype 10A, preferably serotypes selected from the group consisting of serotypes 1, 2, 3, 4, 5, 6A, 6B, 7F, 8, 9N, 9V, 11A, 12F, 13, 14, 15B, 17F, 18C, 19A, 19F, 20, 22F, 23F and 33F, more preferably serotypes selected from the group consisting of serotypes 1, 3, 4, 5, 6A, 6B, 7F, 8, 9N, 9V, 11A, 12F, 14, 15B, 18C, 19A, 19F, 22F, 23F and 33F. Most preferably, "the serotypes except for serotype 10A" can be i) serotypes 1, 3 and 4, ii) serotypes 1, 4, 6A, 6B, 9V and 11A, or iii) serotypes 1, 3, 4, 5, 6A, 6B, 7F, 8, 9N, 9V, 11A, 12F, 14, 15B, 18C, 19A, 19F, 22F, 23F and 33F.

In one embodiment, a solution containing S. pneumoniae of only one serotype (hereinafter referred to as "monovalent S. pneumoniae solution") that is different from the serotype of S. pneumoniae in the step (a) can be mixed in the step (C). In this case, it is possible to check which serotypes of S. pneumoniae cause cross-reactivity by sequentially, and respectively mixing monovalent S. pneumoniae solution of all serotypes that is different from the serotypes of S. pneumoniae in the step (a).

As an example, when serotype 10A S. pneumoniae was administered to the subject in the step (a) to obtain serum, in step (c), serotypes causing cross-reactivity can be determined by sequentially and respectively mixing monovalent S. pneumoniae solutions of remaining serotypes except for serotype 10A into the serum. More specifically, serotypes causing cross-reactivity can be determined by sequentially and respectively mixing monovalent S. pneumoniae solutions of all serotypes except for serotype 10A, preferably, monovalent S. pneumoniae solutions of serotypes 1, 2, 3, 4, 5, 6A, 6B, 7F, 8, 9N, 9V, 11A, 12F, 13, 14, 15B, 17F, 18C, 19A, 19F, 20, 22F, 23F and 33F, more preferably, 1, 3, 4, 5, 6A, 6B, 7F, 8, 9N, 9V, 11A, 12F, 14, 15B, 18C, 19A, 19F, 22F, 23F and 33F.

In another embodiment, a solution containing S. pneumoniae of two or more serotypes (hereinafter referred to as "multivalent S. pneumoniae solution") that is different from the serotype of S. pneumoniae in the step (a) can be mixed in the step (C). In this case, eventually, the serum is preferably mixed at least once with S. pneumoniae of all serotypes that is different from the S. pneumoniae in the step (a). Preferably, the presence or absence of cross-reactivity can be confirmed by mixing the serum with multivalent S. pneumoniae solution containing all serotypes of S. pneumoniae among serotypes 1, 2, 3, 4, 5, 6A, 6B, 7F, 8, 9N, 9V, 10A, 11A, 12F, 13, 14, 15B, 17F, 18C, 19A, 19F, 20, 22F, 23F and 33F except for the serotype used in the step (a). More preferably, the presence or absence of cross-reactivity can be confirmed by mixing the serum with multivalent S. pneumoniae solution containing all serotypes of S. pneumoniae among serotypes 1, 3, 4, 5, 6A, 6B, 7F, 8, 9N, 9V, 10A, 11A, 12F, 14, 15B, 18C, 19A, 19F, 22F, 23F and 33F except for the serotype used in the step (a).

Meanwhile, when the cross-reactivity is absent as a result of mixing the bivalent or more multivalent S. pneumoniae solution to the serum, it can be determined that antibodies recognizing the S. pneumoniae capsular polysaccharide of the serotypes contained in the multivalent S. pneumoniae solution as an antigen are not contained in the serum.

On the contrary, when cross-reactivity occurs, it can be determined that antibodies recognizing the S. pneumoniae capsular polysaccharide of the serotypes contained in the multivalent S. pneumoniae solution as an antigen are contained in the serum. In this case, the serotypes of S. pneumoniae causing the cross-reactivity can be confirmed by sequentially and respectively mixing the serum with monovalent S. pneumoniae solutions of each serotype that is contained in the multivalent S. pneumoniae solution.

As used herein, the term "monovalent S. pneumoniae solution" refers to a solution containing S. pneumoniae of any one serotype. For example, a solution containing serotype 10A S. pneumoniae can be defined as "10A monovalent S. pneumoniae solution". In one example of the present invention, a monovalent S. pneumoniae solution containing 6.6 ug/mL of S. pneumoniae capsular polysaccharide of the specific serotype was defined as a "monovalent standard stock solution". The S. pneumoniae contained in the monovalent S. pneumoniae solution can be live S. pneumoniae, inactivated S. pneumoniae or live attenuated S. pneumoniae, and preferably inactivated S. pneumoniae or live attenuated S. pneumoniae. And, most preferably, it can be inactivated S. pneumoniae.

As used herein, the term "multivalent S. pneumoniae solution" refers to a solution containing two or more serotypes of S. pneumoniae. As an example, a solution containing S. pneumoniae of serotypes 1, 2, 3, 4, 5, 6A, 6B, 7F, 8, 9N, 9V, 10A, 11A, 12F, 13, 14, 15B, 17F, 18C, 19A, 19F, 20, 22F, 23F and 33F can be defined as "25-valent S. pneumoniae solution". In one example of the present invention, a multivalent S. pneumoniae solution containing 6.6 ug/mL of each S. pneumoniae capsular polysaccharide of serotypes respectively was defined as a "multivalent standard stock solution". The S. pneumoniae contained in the multivalent S. pneumoniae solution can be live S. pneumoniae, inactivated S. pneumoniae or live attenuated S. pneumoniae, and preferably inactivated S. pneumoniae or live attenuated S. pneumoniae. And, most preferably, it can be inactivated S. pneumoniae.

As used herein, the term "cross-reactivity" refers to an aggregation reaction by antigen-antibody reaction, and refers to an aggregation reaction by reaction between antibodies presented in a antiserum against a S. pneumoniae of specific serotype obtained in the step (B) with capsular polysaccharide of S. pneumoniae of serotypes that is different from the specific serotype above, when the antiserum recognizes the capsular polysaccharide as an antigen. The cross-reactivity can be confirmed with naked eyes, preferably through nephelometry.

In one embodiment, the "S. pneumoniae of different serotypes from S. pneumoniae in the step (a)" can be inactivated S. pneumoniae or live attenuated S. pneumoniae, and it is as described above.

(d) Removing an Aggregated Complex Induced by Cross-Reactivity

In the method of the present invention, the step (d) is a step of completing the antiserum having a very high specificity for a specific serotype by removing the cross-reactivity when it is confirmed in the step (c).

Removing the cross-reactivity in the step (d) of the present invention is to remove antibodies that recognize S. pneumoniae capsular polysaccharide of other serotypes other than the serotype of S. pneumoniae in the step (a) as an antigen.

As a result of mixing the serum obtained in the step (b) with monovalent or multivalent S. pneumoniae solution, when cross-reactivity, that is, aggregation reaction occurs, aggregated complex(agglutination) subsides. An antiserum from which cross-reactivity has been removed can be obtained by immersing this aggregated complex completely through centrifugation and then taking the supernatant or by removing the aggregated complex by filtration.

In one embodiment, in the step (c), if monovalent S. pneumoniae solutions of each serotype are sequentially mixed with the serum to confirm the presence or absence of cross-reactivity, a large amount of the monovalent S. pneumoniae solution of certain serotype which cause cross-reactivity can be mixed. After then, monovalent S. pneumoniae solution of the remaining serotypes can be mixed sequentially to confirm additional cross-reactivity occur. In this way, cross-reactivity with all serotypes can be removed completely.

In another embodiment, in the step (c), if multivalent S. pneumoniae solutions of serotypes are sequentially mixed with the serum to confirm the presence or absence of cross-reactivity, a large amount of the multivalent S. pneumoniae solution which cause cross-reactivity can be mixed to remove aggregated complex completely. Or, after identifying the serotypes of S. pneumoniae causing cross-reactivity by using monovalent S. pneumoniae solutions, the aggregated complex can be completely removed by mixing the serum with a large amount of the monovalent S. pneumoniae solutions.

In another embodiment, the process of removing the cross-reactivity can be performed repeatedly. Specifically, the aggregated complex can be removed by centrifugation or filtration after excessively mixing monovalent S. pneumoniae solution of serotype in which the cross-reactivity was confirmed, and then again aggregated complex can be removed by mixing the same monovalent S. pneumoniae solution.

Meanwhile, after the step (d), the step (e) of confirming whether or not the cross-reactivity is removed by conducting nephelometry after mixing the S. pneumoniae in the step (c) with antiserum from which the aggregated complex has been removed in the step (d) can be further performed.

Specifically, a monovalent or multivalent *S. pneumoniae* solution is mixed with the serum, and then the serum is analyzed by the nephelometry. And then, whether cross-reactivity is completely removed or not can be confirmed by comparing the nephelometric result value with the nephelometric result value of blank sample or monovalent *S. pneumoniae* solution of 1.0 ug/mL measured by the same nephelometry.

As an example, when the nephelometric result value of antiserum is less than "the average nephelometric result value of the blank sample", less than "the average nephelometric result value of the blank sample+standard deviation", less than "the average nephelometric result value of the blank sample+(2×standard deviation)", less than "the average nephelometric result value of the blank sample+(3× standard deviation)" or less than the nephelometric result value of monovalent *S. pneumoniae* solution of 1.0 ug/mL, it can be determined that the cross-reactivity is completely removed.

Or, the antiserum can be mixed repeatedly with *S. pneumoniae* of serotype, the serotype of which is confirmed to induce cross-reactivity in the step (c), followed by removing aggregated complexes until the nephelometric result value satisfies any one or more of the following (i) and (ii):

(i) less than the nephelometric result value of 1.0 ug/ml of *S. pneumoniae*, the serotype of which is confirmed to induce cross-reactivity in the step (c), and (ii) less than the average nephelometric result value of blank+(3×standard deviation).

The antiserum obtained by administering *S. pneumoniae* to a subject contains not only antibodies against *S. pneumoniae* capsular polysaccharides, but also antibodies against cell wall polysaccharide or capsular proteins present in all serotypes of *S. pneumoniae*. By the way, the method of the present invention comprising the steps (a) to (d) can improve the specificity of antiserum against a specific serotype, because the method of the present invention removes cross-reactivity using *S. pneumoniae*, inactivated *S. pneumoniae*, or live attenuated *S. pneumoniae* itself, thereby removing not only antibodies causing cross-reactivity with *S. pneumoniae* capsular polysaccharides, but also antibodies causing cross-reactivity with the cell wall polysaccharides or capsular proteins.

In addition, in the step of removing cross-reactivity, there is a great advantage in terms of the manufacturing process because the cross-reactivity can be thoroughly removed by a very simple method such as centrifugation or filtration without the help of a separate complicated procedure or equipment.

The present invention provides an antiserum of *Streptococcus pneumoniae* prepared according to the method above.

In the present invention, the antiserum is preferably an antiserum against *S. pneumoniae* of serotype selected from the group consisting of serotypes 1, 2, 3, 4, 5, 6A, 6B, 7F, 8, 9N, 9V, 10A, 11A, 12F, 13, 14, 15B, 17F, 18C, 19A, 19F, 20, 22F, 23F and 33F, more preferably, selected from the group consisting of serotypes 1, 3, 4, 5, 6A, 6B, 7F, 8, 9N, 9V, 10A, 11A, 12F, 14, 15B, 18C, 19A, 19F, 22F, 23F and 33F. In one example of the present invention, the antiserum, from which cross-reactivity was removed, against *S. pneumoniae* of serotype 1, 3, 4, 5, 6A, 6B, 7F, 8, 9N, 9V, 10A, 11A, 12F, 14, 15B, 18C, 19A, 19F, 22F, 23F or 33F.

As an example, in the case of the antiserum, from which cross-reactivity was removed, against serotype 1 *S. pneumoniae*, it can be the antiserum from which cross-reactivity with *S. pneumoniae* of serotype 3, 4, 5, 6A, 6B, 7F, 8, 9N, 9V, 10A, 11A, 12F, 14, 15B, 18C, 19A, 19F, 22F, 23F or 33F is removed.

In the case of the antiserum, from which cross-reactivity was removed, against serotype 3 *S. pneumoniae*, it can be the antiserum from which cross-reactivity with *S. pneumoniae* of serotype 1, 4, 5, 6A, 6B, 7F, 8, 9N, 9V, 10A, 11A, 12F, 14, 15B, 18C, 19A, 19F, 22F, 23F or 33F is removed.

In the case of the antiserum, from which cross-reactivity was removed, against serotype 4 *S. pneumoniae*, it can be the antiserum from which cross-reactivity with *S. pneumoniae* of serotype 1, 3, 5, 6A, 6B, 7F, 8, 9N, 9V, 10A, 11A, 12F, 14, 15B, 18C, 19A, 19F, 22F, 23F or 33F is removed.

In the case of the antiserum, from which cross-reactivity was removed, against serotype 5 *S. pneumoniae*, it can be the antiserum from which cross-reactivity with *S. pneumoniae* of serotype 1, 3, 4, 6A, 6B, 7F, 8, 9N, 9V, 10A, 11A, 12F, 14, 15B, 18C, 19A, 19F, 22F, 23F or 33F is removed.

In the case of the antiserum, from which cross-reactivity was removed, against serotype 6A *S. pneumoniae*, it can be the antiserum from which cross-reactivity with *S. pneumoniae* of serotype 1, 3, 4, 5, 6B, 7F, 8, 9N, 9V, 10A, 11A, 12F, 14, 15B, 18C, 19A, 19F, 22F, 23F or 33F is removed.

In the case of the antiserum, from which cross-reactivity was removed, against serotype 6B *S. pneumoniae*, it can be the antiserum from which cross-reactivity with *S. pneumoniae* of serotype 1, 3, 4, 5, 6A, 7F, 8, 9N, 9V, 10A, 11A, 12F, 14, 15B, 18C, 19A, 19F, 22F, 23F or 33F is removed.

In the case of the antiserum, from which cross-reactivity was removed, against serotype 7F *S. pneumoniae*, it can be the antiserum from which cross-reactivity with *S. pneumoniae* of serotype 1, 3, 4, 5, 6A, 6B, 8, 9N, 9V, 10A, 11A, 12F, 14, 15B, 18C, 19A, 19F, 22F, 23F or 33F is removed.

In the case of the antiserum, from which cross-reactivity was removed, against serotype 8 *S. pneumoniae*, it can be the antiserum from which cross-reactivity with *S. pneumoniae* of serotype 1, 3, 4, 5, 6A, 6B, 7F, 9N, 9V, 10A, 11A, 12F, 14, 15B, 18C, 19A, 19F, 22F, 23F or 33F is removed.

In the case of the antiserum, from which cross-reactivity was removed, against serotype 9N *S. pneumoniae*, it can be the antiserum from which cross-reactivity with *S. pneumoniae* of serotype 1, 3, 4, 5, 6A, 6B, 7F, 8, 9V, 10A, 11A, 12F, 14, 15B, 18C, 19A, 19F, 22F, 23F or 33F is removed.

In the case of the antiserum, from which cross-reactivity was removed, against serotype 9V *S. pneumoniae*, it can be the antiserum from which cross-reactivity with *S. pneumoniae* of serotype 1, 3, 4, 5, 6A, 6B, 7F, 8, 9N, 10A, 11A, 12F, 14, 15B, 18C, 19A, 19F, 22F, 23F or 33F is removed.

In the case of the antiserum, from which cross-reactivity was removed, against serotype 10A *S. pneumoniae*, it can be the antiserum from which cross-reactivity with *S. pneumoniae* of serotype 1, 3, 4, 5, 6A, 6B, 7F, 8, 9N, 9V, 11A, 12F, 14, 15B, 18C, 19A, 19F, 22F, 23F or 33F is removed.

In the case of the antiserum, from which cross-reactivity was removed, against serotype 11A *S. pneumoniae*, it can be the antiserum from which cross-reactivity with *S. pneumoniae* of serotype 1, 3, 4, 5, 6A, 6B, 7F, 8, 9N, 9V, 10A, 12F, 14, 15B, 18C, 19A, 19F, 22F, 23F or 33F is removed.

In the case of the antiserum, from which cross-reactivity was removed, against serotype 12F *S. pneumoniae*, it can be the antiserum from which cross-reactivity with *S. pneumoniae* of serotype 1, 3, 4, 5, 6A, 6B, 7F, 8, 9N, 9V, 10A, 11A, 14, 15B, 18C, 19A, 19F, 22F, 23F or 33F is removed.

In the case of the antiserum, from which cross-reactivity was removed, against serotype 14 *S. pneumoniae*, it can be the antiserum from which cross-reactivity with *S. pneumo-

*niae* of serotype 1, 3, 4, 5, 6A, 6B, 7F, 8, 9N, 9V, 10A, 11A, 12F, 15B, 18C, 19A, 19F, 22F, 23F or 33F is removed.

In the case of the antiserum, from which cross-reactivity was removed, against serotype 15B *S. pneumoniae*, it can be the antiserum from which cross-reactivity with *S. pneumoniae* of serotype 1, 3, 4, 5, 6A, 6B, 7F, 8, 9N, 9V, 10A, 11A, 12F, 14, 18C, 19A, 19F, 22F, 23F or 33F is removed.

In the case of the antiserum, from which cross-reactivity was removed, against serotype 18C *S. pneumoniae*, it can be the antiserum from which cross-reactivity with *S. pneumoniae* of serotype 1, 3, 4, 5, 6A, 6B, 7F, 8, 9N, 9V, 10A, 11A, 12F, 14, 15B, 19A, 19F, 22F, 23F or 33F is removed.

In the case of the antiserum, from which cross-reactivity was removed, against serotype 19A *S. pneumoniae*, it can be the antiserum from which cross-reactivity with *S. pneumoniae* of serotype 1, 3, 4, 5, 6A, 6B, 7F, 8, 9N, 9V, 10A, 11A, 12F, 14, 15B, 18C, 19F, 22F, 23F or 33F is removed.

In the case of the antiserum, from which cross-reactivity was removed, against serotype 19F *S. pneumoniae*, it can be the antiserum from which cross-reactivity with *S. pneumoniae* of serotype 1, 3, 4, 5, 6A, 6B, 7F, 8, 9N, 9V, 10A, 11A, 12F, 14, 15B, 18C, 19A, 22F, 23F or 33F is removed.

In the case of the antiserum, from which cross-reactivity was removed, against serotype 22F *S. pneumoniae*, it can be the antiserum from which cross-reactivity with *S. pneumoniae* of serotype 1, 3, 4, 5, 6A, 6B, 7F, 8, 9N, 9V, 10A, 11A, 12F, 14, 15B, 18C, 19A, 19F, 23F or 33F is removed.

In the case of the antiserum, from which cross-reactivity was removed, against serotype 23F *S. pneumoniae*, it can be the antiserum from which cross-reactivity with *S. pneumoniae* of serotype 1, 3, 4, 5, 6A, 6B, 7F, 8, 9N, 9V, 10A, 11A, 12F, 14, 15B, 18C, 19A, 19F, 22F or 33F is removed.

In the case of the antiserum, from which cross-reactivity was removed, against serotype 33F *S. pneumoniae*, it can be the antiserum from which cross-reactivity with *S. pneumoniae* of serotype 1, 3, 4, 5, 6A, 6B, 7F, 8, 9N, 9V, 10A, 11A, 12F, 14, 15B, 18C, 19A, 19F, 22F or 23F is removed.

The above examples are provided to help understanding of the present invention, but are not limited thereto.

The antiserum from which cross-reactivity has been removed specifically binds to the serotypes of *S. pneumoniae* acting as an antigen and does not react with other serotypes of *S. pneumoniae*. Therefore, when the antiserum from which the cross-reaction is removed is used in an assay for quantifying *S. pneumoniae* of each serotype, the accuracy of the assay can be increased.

In addition, the antiserum from which cross-reactivity has been removed includes antibodies which do not cross-react with epitopes present in *S. pneumoniae* of other serotypes among the antibodies against the epitopes present in the *S. pneumoniae* acting as an antigen. Specifically, the antiserum from which the cross-reactivity has been removed can include antibodies which do not cross-react with the capsular polysaccharide present in *S. pneumoniae* of other serotypes among the antibodies against the capsular polysaccharide present in the *S. pneumoniae* acting as an antigen.

The present invention provides a pharmaceutical composition for preventing or treating infectious diseases caused by *Streptococcus pneumoniae*, the composition comprising the antiserum of above as an active ingredient The pharmaceutical composition of the present invention comprises a large amount of antibodies against *S. pneumoniae* of a specific serotype. Therefore, it can be used for serotherapy against infectious disease of *S. pneumoniae*, preferably, initial phase of infectious disease of *S. pneumoniae*.

In particular, since the antiserum as an active ingredient of the pharmaceutical composition of the present invention is antiserum to a specific serotype, it may be more usefully used when the serotype of *S. pneumoniae* infected to a patient is accurately identified.

The pharmaceutical composition according to the present invention may comprise antiserum of *S. pneumoniae* alone or be formulated in a suitable form with a pharmaceutically acceptable carrier and may further contain excipients or diluents. As used herein, 'pharmaceutically acceptable' refers to a non-toxic composition that is physiologically acceptable and does not cause an allergic reaction, such as gastrointestinal disorders, dizziness, or the like, when administered to a human being.

Pharmaceutically acceptable carriers may further include, for example, carriers for oral administration or carriers for parenteral administration. Carriers for oral administration may include lactose, starch, cellulose derivatives, magnesium stearate, stearic acid and the like. In addition, it may include various drug delivery materials used for oral administration to the peptide formulation. In addition, carriers for parenteral administration may include water, suitable oils, saline, aqueous glucose and glycols, and the like, and may further include stabilizers and preservatives. Suitable stabilizers include antioxidants such as sodium hydrogen sulfite, sodium sulfite or ascorbic acid. Suitable preservatives include benzalkonium chloride, methyl- or propyl-parabens and chlorobutanol. The pharmaceutical composition of the present invention may further include a lubricant, a humectant, a sweetener, a flavoring agent, an emulsifier, a suspension agent, and the like in addition to the above components. Other pharmaceutically acceptable carriers and agents may be referred to those described in Remington's Pharmaceutical Sciences, 19th ed., Mack Publishing Company, Easton, PA, 1995.

The composition of the present invention can be administered to any mammal, including humans. For example, it can be administered orally or parenterally. Parenteral administration methods include, but are not limited to, intravenous, intramuscular, intraarterial, intramedullary, intradural, intracardiac, transdermal, subcutaneous, intraperitoneal, intranasal, intestinal, topical, sublingual or rectal administration.

The pharmaceutical composition of the present invention can be formulated into a preparation for oral or parenteral administration according to the route of administration as described above.

In the case of preparations for oral administration, the compositions of the present invention may be formulated using methods known in the art as powders, granules, tablets, pills, sugarcoated pills, capsules, solutions, gels, syrups, slurries, suspensions and the like. For example, oral preparations can be obtained by tablets or sugarcoated pills by combining the active ingredients with solid excipients and then grinding them, adding suitable auxiliaries and processing them into granule mixtures. Examples of suitable excipients include sugars, including lactose, dextrose, sucrose, sorbitol, mannitol, xylitol, erythritol and maltitol and starch, cellulose, starch including corn starch, wheat starch, rice starch and potato starch, and the like. Fillers such as cellulose, gelatin, polyvinylpyrrolidone and the like, including methyl cellulose, sodium carboxymethylcellulose, hydroxypropylmethyl-cellulose and the like. In addition, crosslinked polyvinylpyrrolidone, agar, alginic acid or sodium alginate and the like may optionally be added as a disintegrant. Furthermore, the pharmaceutical composition of the present invention may further include an anticoagulant, a lubricant, a humectant, a perfume, an emulsifier, a preservative, and the like.

Formulations for parenteral administration can be formulated by methods known in the art in the form of injections, creams, lotions, external ointments, oils, humectants, gels, aerosols and nasal inhalants. These formulations are described in Remington's Pharmaceutical Science, 19th ed., Mack Publishing Company, Easton, PA, 1995, a prescription generally known for all pharmaceutical chemistry.

The total effective amount of the composition of the present invention can be administered to a patient in a single dose and can be administered by a divided treatment protocol that is administered in multiple doses for a long time. The pharmaceutical composition of the present invention can vary the content of the active ingredient depending on the extent of the disease. Preferably the preferred total dose of the pharmaceutical composition of the present invention can be about 0.01 μg to 10,000 mg, most preferably 0.1 μg to 500 mg per kg of patient body weight per day. However, the dosage of the pharmaceutical composition is determined in consideration of various factors such as the formulation method, route of administration and frequency of treatment, as well as various factors such as the patient's age, weight, health status, sex, severity of the disease, diet and excretion rate. In view of this, one of ordinary skill in the art will be able to determine the appropriate effective dosage of the compositions of the present invention. The pharmaceutical composition according to the present invention is not particularly limited to its formulation, route of administration and method of administration as long as the effect of the present invention is shown.

In the present invention, the infectious diseases caused by *Streptococcus pneumoniae* can be pneumonia, bacteremia, meningitis, otitis media, sepsis or sinusitis, but is not limited thereto.

The present invention also provides a composition for diagnosing infectious diseases caused by *S. pneumoniae*, the composition comprising the antiserum above.

The composition for diagnosing infectious diseases caused by *S. pneumoniae* according to the present invention includes antiserum that binds to the capsular polysaccharide of *S. pneumoniae* of a particular serotype, and infectious diseases caused by *S. pneumoniae* can be diagnosed by confirming whether the antiserum binds to certain serotypes of *S. pneumoniae*. At this time, the binding of the antiserum and the certain serotype of *S. pneumoniae* capsular polysaccharides can be confirmed by nephelometry.

Since the composition for diagnosing according to the present invention contains antiserum with a very high specificity for a specific serotype as a main component, the serotype of *S. pneumoniae* that causes an infectious disease can be accurately determined, and accurate diagnosis is possible. This is very advantageous in that it can provide useful information, such as the selection of therapeutic agents for infectious diseases.

The composition for diagnosing of the present invention can be provided in the form of a kit. The kit can include one or more other components or detection devices necessary to identify the serotype of *S. pneumoniae* capsular polysaccharide combined with antiserum. Specifically, the kit for diagnosing *S. pneumoniae* infectious disease according to the present invention may include an antiserum combined with a fluorescent material for generating detectable fluorescence and a detection device capable of detecting fluorescence generated from the antiserum. In addition, it may further include a correction means for correcting the fluorescence value measured by the detection device.

The infectious diseases caused by *S. pneumoniae* is as described above.

The present invention also provides a composition for quantifying antigens of *Streptococcus pneumoniae*, the composition comprising the antiserum above.

The composition for quantifying antigens of *Streptococcus pneumoniae* can be used for quality control of *S. pneumoniae* polysaccharide vaccine, *S. pneumoniae* conjugate vaccine, or meningococcal conjugate vaccine, in which various antigens are present in a sample.

That is, by reacting the composition for quantifying antigens of the present invention with a sample such as a vaccine and analyzing the degree of aggregation reaction through nephelometry, it can be confirmed that the content of the antigen contained in the sample is accurately measured and the finished product of each vaccine satisfies criteria.

The present invention also provides a method for quantifying antigens of *Streptococcus pneumoniae*, the method comprising the steps of:

(a) reacting standard samples with the *Streptococcus pneumoniae* antiserum above, wherein the antigen amount of the standard samples is specified;

(b) analyzing the turbidity of the standard samples resulting from the reaction of step (a) and obtaining a standard curve;

(c) reacting a sample to be detected with the *Streptococcus pneumoniae* antiserum above; and (d) analyzing the turbidity of the sample to be detected resulting from the reaction in the step (c) and calculating the quantity of the antigens by applying the turbidity to the standard curve.

(a) Reacting Standard Samples with the *Streptococcus pneumoniae* Antiserum Above, Wherein the Antigen Amount of the Standard Samples is Specified;

In the step (a), the standard samples mean a sample in which the exact amount of the *S. pneumoniae* antigen of the serotype to be detected is precisely determined. The commercially available one can be used or the one in which the amount of the antigen is accurately determined through various methods can be used.

The antiserum is prepared according to the above-described method of the present invention and means an antiserum obtained by removing cross-reactivity with other serotypes of *S. pneumoniae*. In addition, it means a *S. pneumoniae* antiserum of the same serotype as the serotype of *S. pneumoniae* antigen contained in the standard sample.

(b) Analyzing the Turbidity of the Standard Samples Resulting from the Reaction of Step (a) and Obtaining a Standard Curve;

When the standard samples and the antiserum are reacted in the step (a), an antigen-antibody reaction occurs and cause aggregation, and the aggregation causes a change in turbidity of the sample. Aggregation due to the antigen-antibody reaction is changed according to the reaction amount of the antigen and the antibody contained in the sample. Therefore, a standard curve that represents the quantitative relationship between the amount of the antigen and turbidity can be obtained by analyzing the interrelation between the turbidity of the sample and the amount of the antigen contained in the standard samples.

In the present invention, the standard curve can be applied in the same manner as a conventional standard curve preparation method used for quantitative analysis in the art, for example, standard samples, the amount of antigen of which is specified, are diluted to a concentration of 1 to 10 sections, preferably to a concentration of 3 to 8 sections, and more preferably to a concentration of 4 to 7 sections. And by analyzing the turbidity according to the reaction between each concentration of the standard samples and the antiserum, the standard curve representing the quantitative relationship between the amount of the antigen and turbidity can be obtained.

If the standard curve is not accurately obtained in the antigen quantification method of the present invention, it is not possible to accurately calculate the amount of antigen contained in the sample to be detected in the following steps (c) and (d). Therefore, after clarifying the factors that may affect the accuracy of the standard curve in steps (a) and (b), it is very important to set the optimum conditions through repeated experiments. For example, factors that may affect the accuracy of the standard curve include the concentration range of the standard sample, the amount of buffer used for the experiment, the titer of the antiserum, the dilution factor of the antiserum, antigen-antibody reaction time, reaction temperature, and the like.

The method of analyzing the turbidity in the step (b) is not particularly limited, and any method currently used or newly developed in the art for analyzing turbidity of a sample in the art is applicable to the step (b) of the present invention. It will be apparent to one skilled in the art. Non-limiting examples of the method for analyzing the turbidity include absorbance, transmittance or nephelometry, and preferably it can be nephelometry.

(c) Reacting a Sample to be Detected with the *Streptococcus pneumoniae* Antiserum Above;

In the present invention, the step (c) is a step of inducing an antigen-antibody aggregation reaction by reacting *S. pneumoniae* antiserum with a sample to be detected or suspected of containing antigens of *S. pneumoniae*.

The *S. pneumoniae* antiserum in the step (c) is the same antiserum as the antiserum in the step (a), and antigen-antibody aggregation occur when the sample to be detected contains the same serotype of *S. pneumoniae* or its antigenic protein as the serotype of the antiserum. Then, the turbidity of the sample to be detected is changed by the antigen-antibody aggregation reaction.

In this case, the conditions for reacting the sample to be detected with antiserum in the step (c) are preferably the same as the conditions for reacting the standard sample with antiserum in the step (a).

In the present invention, the sample to be detected means a sample containing or suspected of containing *S. pneumoniae* of the serotype to be detected or an antigen thereof, and the range is not particularly limited, but it can be biological samples of vaccine compositions such as tissue, cells, whole blood, plasma, serum, blood, saliva, synovial fluid, urine, sputum, lymph, intercellular fluid, and the like.

In the case where the sample to be detected is a biological sample derived from an individual, it may be possible to diagnose an infection, predict the prognosis, and set a treatment strategy through antigen quantification. When the sample to be detected is vaccine compositions, accurate amount of antigen content can be analyzed, thereby confirming whether the finished product of each vaccine meets criteria.

(d) Analyzing the Turbidity of the Sample Resulting from the Reaction in the Step (c) and Calculating the Quantity of the Antigens by Applying the Turbidity to the Standard Curve;

The step (d) is a step of calculating the amount of antigen contained in the sample to be detected by applying to the standard curve created in the step (b).

The method of analyzing the turbidity in the step (d) may be the same as described in the step (b).

The method of calculating the amount of antigen by substituting the turbidity according to the reaction between the sample to be detected and antiserum into the standard curve prepared in the step (b) can be easily applied by a person skilled in the art according to the format of the standard curve.

As described above, the method for quantifying antigens of the present invention utilizes the antiserum of the present invention, in which cross-reactivity are eliminated. The advantage is that it can be quantified with high accuracy.

The present invention provides use of the antiserum of *Streptococcus pneumoniae* for preparing an agent for preventing or treating infectious diseases caused by *Streptococcus pneumoniae*.

The present invention provides a method for treating infectious diseases caused by *Streptococcus pneumoniae* in a subject, the method comprising administering an effective amount of a composition comprising, as an active ingredient, the antiserum of *Streptococcus pneumoniae* to the subject in need thereof.

The present invention provides use of the antiserum of *Streptococcus pneumoniae* for preparing an agent for diagnosing infectious diseases caused by *Streptococcus pneumoniae*.

The present invention provides use of the antiserum of *Streptococcus pneumoniae* for preparing an agent for quantifying antigens of *Streptococcus pneumoniae*.

The term 'effective amount' of the present invention means an amount which exhibits effects of improving, treating, preventing, detecting, diagnosing of neurodegenerative diseases, or inhibiting or alleviating neurodegenerative diseases when administered to the subject. The 'subject' may be animals, preferably, mammals, particularly animals including humans and may also be cells, tissues, and organs derived from animals. The subject may be a patient requiring the effects.

The term 'treatment' of the present invention comprehensively refers to improving neurodegenerative diseases or symptoms of neurodegenerative diseases, and may include treating or substantially preventing these diseases, or improving the conditions thereof and includes alleviating, treating or preventing a symptom or most of symptoms derived from neurodegenerative diseases, but is not limited thereto.

The term 'comprising' of the present invention is used in the same manner as 'containing' or 'characterizing', and does not exclude additional ingredients or steps of the method which are not mentioned in the composition or the method. The term 'consisting of' means excluding additional elements, steps or ingredients, etc., unless otherwise noted. The term 'essentially consisting of' means including ingredients or steps that do not substantially affect basic properties thereof in addition to the described ingredients or steps within the scope of the composition or the method.

Advantageous Effects of Invention

The *Streptococcus pneumoniae* antiserum prepared according to the method of the present invention has very high specificity for a particular serotype, since the cross-reactivity with *S. pneumoniae* of serotypes expressing capsular polysaccharides of similar structure is removed. Therefore, it can be very useful in the related art that requires accurate quantification of S. pneumoniae capsular polysaccharide.

MODE FOR THE INVENTION

Hereinafter, the present invention will be described in detail.

However, the following examples are merely for illustrating the present invention and are not intended to limit the scope of the present invention.

Example 1. Preparation of S. pneumoniae Vaccine

S. pneumoniae culture was performed by methods known to those skilled in the art. S. pneumoniae of each serotypes (serotypes 1, 3, 4, 5, 6A, 6B, 7F, 8, 9N, 9V, 10A, 11A, 12F, 14, 15B, 18C, 19A, 19F, 22F, 23F and 33F) were obtained from depository authorities such as ATCC, JCM, KCCM, schools, and institutions. S. pneumoniae were identified by capsular and non-motile, gram-positive, lancet-shaped diplococci and hemolysis in the blood agar media. Serotypes were identified using the Quellung test using specific antiserum.

To increase S. pneumoniae and remove components of animal origin, seed stocks were cultured in F1, F2, and F3 generations. In addition, the seed stocks were further cultured for two generations. Additional first generations were cultured from F3 vials and subsequent generations were cultured from additional first generation vials. Seed vials were cryopreserved at −70° C. or lower with synthetic glycerol as cryopreservative. For strain bank preparation, all cultures were grown in soy-based medium. Prior to freezing, the strain was concentrated by centrifugation and the medium used was removed, and then the strain pellets were resuspended in fresh medium containing synthetic glycerol.

The S. pneumoniae of respective serotypes for preparing S. pneumoniae vaccine were inoculated to the flasks containing a soybean-based medium of pH 7.0±8.2 (pH 8.1±0.1 for serotypes 4, 9N, 9V, 12F, and pH 7.5±0.1 for serotype 14), followed by incubating for 10 to 12 hours in a 36±2° C., 5% $CO_2$ incubator without agitation until the absorbance ($O.D._{600}$) reaches at least 0.5. After the incubation, the flasks were checked for contamination by a microscope. Thereafter, a seed flask was used to inoculate the culture fermenter containing the soy-based medium. The pH of the culture was maintained using 3N NaOH, and cultured for 4 to 12 hours so that the absorbance (O.D.600) became 0.6 to 1.0 depending on the serotypes of S. pneumoniae.

37% (v/v) formaldehyde was added so as to have a final concentration of 0.5 to 2% (v/v), homogenized for 30 minutes, and then inactivated at room temperature overnight. The inactivated culture was centrifuged for 30 minutes at 4° C. However, serotype 3 was centrifuged for 40 minutes. Thereafter, the supernatant was discarded and the pellets were collected. Then, Sorensen Buffer (phosphate buffer, formaldehyde) was added and suspended and stored at a temperature of 2 to 8° C.

The suspension of inactivated S. pneumoniae was appropriately diluted with 0.9% (w/v) sodium chloride or water for injection to obtain a S. pneumoniae vaccine stock solution of each serotype, and stored at 2 to 8° C. The absorbance ($O.D._{600}$) value and dose of the S. pneumoniae vaccine stock solution were recorded, and an inactivation test, gram staining, and swelling test were performed.

S. pneumoniae vaccine for animal inoculation was prepared by diluting the S. pneumoniae vaccine stock solution with Sorensen Buffer such that the absorbance ($O.D._{600}$) was 4.0 or less, and stored at 2 to 8° C.

In addition, the S. pneumoniae vaccines for adsorption for each serotype to remove the cross-reactivity of antiserum were prepared by diluting the S. pneumoniae vaccine stock solution with Sorensen Buffer so that the absorbance ($O.D._{600}$) was 4.0 or higher and stored at 2 to 8° C.

Example 2. Preparation of Standard Solution for Analyzing Antibody Titer of Antiserum and Cross-Reactivity In order to confirm the antibody titer and the presence of absence of cross-reactivity of the antiserum, multivalent standard stock solutions and multivalent standard solutions were prepared. The multivalent standard stock solutions were prepared by diluting or mixing monovalent stock solutions having known concentrations, and the multivalent standard solutions were prepared by diluting the multivalent standard stock solutions. The monovalent solutions refer to monovalent bulk produced for each serotype of S. pneumoniae.

A multivalent (21-valent) standard stock solution was prepared by mixing monovalent stock solutions of serotypes 1, 3, 4, 5, 6A, 6B, 7F, 8, 9N, 9V, 10A, 11A, 12F, 14, 15B, 18C, 19A, 19F, 22F, 23F and 33F, respectively, wherein the multivalent standard stock solution comprises capsular polysaccharide of each serotype at a concentration of 6.6 μg/ml. The amount of monovalent stock solution required for each serotype on the basis of 100 ml was calculated and place it in a plastic container, and then sample dilution buffer (0.85% (v/v) sodium chloride/5 mM succinic acid/0.02% (v/v), polysorbate 80/1 mg/ml aluminum phosphate, pH 5.8) was added so that the total volume became 100 ml. Thereafter, the 21-valent standard solution was stirred and mixed at room temperature for 2 hours or more, and then refrigerated.

In addition, a total of 21 types of monovalent standard stock solutions were prepared by diluting the monovalent stock solutions for each serotype so that the concentration of capsular polysaccharides of each serotype became 6.6 μg/ml. Specifically, after calculating the amount of monovalent stock solution required based on 100 ml and put in a plastic container, the sample dilution buffer was added so that the total volume became 100 ml. At room temperature, the mixture was stirred slowly for 2 hours or more, and then refrigerated.

The monovalent standard solution and the multivalent standard solution were prepared by diluting the monovalent standard stock solution and the multivalent standard stock solution so that the concentrations of the capsular polysaccharides were 1.0, 2.0, 3.0, 4.0, 5.0, and 6.0 μg/ml. Each standard solution was prepared by mixing the dilution buffer and standard stock solution, followed by adding sodium hydroxide solution and citric acid.

Example 3: Preparation of S. pneumoniae Antiserum

Two or three NewZealand White rabbits (Female, 3-4 kg) were immunized for each serotype. The S. pneumoniae vaccine for animal inoculation prepared in Example 1 was warmed at 37° C. for 10 minutes before administration to rabbits. The warmed S. pneumoniae vaccine was administered to the ear vein, and 2 ml of blood was collected from the vein before administration of the vaccine. The collected blood was allowed to stand at room temperature for 1 hour and then left at 4° C. overnight. The following day, the collected blood was centrifuged to separate serum. Antibody titer of serum was analyzed by nephelometry after diluting the serum with dilution buffer (Diluent 1, Beckman Coulter) by 1:3, 1:6, 1:10, and 1:30. Six to seven days after the last immunization day, the serum was obtained from the heart when the response value (Rate unit) of 6-fold diluted serum was 20 to 150.

Inoculation schedules and doses are shown in Table 1 below. After 4 weeks, the immune schedule and dose are the same.

TABLE 1

| Weeks | Dose (㎖/Head) | | | | | | |
|---|---|---|---|---|---|---|---|
| | MON | TUE | WED | THU | FRI | SAT | SUN |
| 1 | 0.1 | 0.2 | 0.2 | Rest | Rest | Rest | Rest |
| 2 | 0.2 | 0.3 | 0.3 | Rest | Rest | Rest | Rest |
| 3 | 0.5 | 0.5 | 0.7 | Rest | Rest | Rest | Rest |
| 4 | bleeding/1.0 | 1.0 | 1.0 | Rest | Rest | Rest | Rest |

The final blood collected from each rabbit's heart was allowed to stand at room temperature for 1 hour and then left at 4° C. overnight. The following day, the collected blood was centrifuged to separate serum. The dose of the final blood serum was recorded and heat treated at 56° C. for 30 minutes, then left at room temperature to drop the temperature. A portion of the heat-treated serum was centrifuged to obtain a supernatant. The antibody titer and the cross-reactivity of the final blood serum were analyzed by nephelometry for monovalent standard stock solution (6.6 ug/mL) of each serotype prepared in Example 2.

Specifically, the antibody titer of the separated serum was analyzed by nephelometry using a monovalent standard stock solution of the serotype according to a conventionally known method.

In addition, in order to confirm the cross-reactivity of the prepared S. pneumoniae antiserum of each serotype, 20 kinds of monovalent standard stock solutions except for the serotype of S. pneumoniae administered to the animals to prepare antiserum were sequentially mixed with each serum. Thereafter, whether antigen-antibody aggregation reaction occurred was analyzed by nephelometry.

If no cross-reactivity was seen, serum of rabbits with an antibody titer of 1 or more was mixed and sodium azide (NaN₃) was added at a concentration of 0.0975% (w/v). Thereafter, the mixture was stirred at room temperature for 40 to 80 rpm for 10 to 15 minutes, and then aseptically filtered using a 0.22 μm filter. The filtered antiserum was aliquoted and stored at 2-8° C.

If cross-reactivity occurs, the serum of rabbits having an antibody titer of 1 or more was mixed, and then reacted with the S. pneumoniae vaccine for adsorption of the serotype causing cross-reactivity. S. pneumoniae vaccines for adsorption were prepared at a ratio of 0.5 to 1.0 of the serum dose, and prepared for all serotypes causing cross-reactivity, respectively. S. pneumoniae vaccine for adsorption was centrifugated and the supernatant was removed, and then the antiserum of rabbit was added to the precipitate and suspended uniformly. After stirring for 30 min at 100-150 rpm conditions at room temperature followed by centrifugation, and the supernatant were collected.

The result of cross-reactivity between antiserum of each serotype and S. pneumoniae vaccines of the serotypes except for the serotype above is shown in Table 2.

TABLE 2

| B | A | | | | | | | | | | | | | | | | | | | |
|---|---|---|---|---|---|---|---|---|---|---|---|---|---|---|---|---|---|---|---|---|
| | 1 | 3 | 4 | 5 | 6A | 6B | 7P | 8 | 9N | 9V | 10A | 11A | 12F | 14 | 15B | 18C | 19A | 19F | 22F | 23F | 33F |
| 12F | O | X | X | X | O | O | X | X | X | X | X | X | | X | X | X | O | X | X | O | X |

A: monovalent stock solution,
B: antiserum

If cross-reactivity occurred with two or more serotypes, the same removal process was repeated one by one. The supernatant obtained after the adsorption process was reconfirmed by nephelometry, and the adsorption process was repeated until the cross-reactivity was removed. Finally, the supernatant obtained was analyzed to confirm whether cross-reactivity by nephelometry. The adsorption process was repeated until the response value of nephelometry satisfies (i) less than the average nephelometric result value of blank+(3×standard deviation) or (ii) less than the nephelometric result value of 1.0 ug/ml of Streptococcus pneumoniae multivalent standard solution.

When the cross-reactivity fell below the criteria above, sodium azide was added to the antiserum at a concentration of 0.0975% (w/v). Thereafter, the mixture was stirred at room temperature for 40 to 80 rpm for 10 to 15 minutes, and then aseptically filtered using a 0.22 μm filter. The filtered antiserum was aliquoted and stored at 2-8° C.

The invention claimed is:

1. A method for preparing antiserum of Streptococcus pneumoniae, the method comprising the steps of:
   (a) administering Streptococcus pneumoniae to a subject;
   (b) collecting a serum from the subject;
   (c) mixing the collected serum with Streptococcus pneumoniae of different serotype from the Streptococcus pneumoniae in the step (a) and confirming the presence or absence of cross-reactivity;
   (d) removing an aggregated complex induced by cross-reactivity, in case where the presence of cross-reactivity is confirmed in the step (c); and
   (e) obtaining the antiserum of which cross-reactivity is removed in the step (d).

2. The method according to claim 1, wherein the step (c) is the step of mixing the collected serum serially with each serotype of *Streptococcus pneumoniae* and confirming the presence or absence of cross-reactivity, wherein the each serotype of *Streptococcus pneumoniae* is different from that of *Streptococcus pneumoniae* in the step (a).

3. The method according to claim 1, wherein the step (c) is the step of mixing the collected serum with two or more serotypes of *Streptococcus pneumoniae* and confirming the presence or absence of cross-reactivity, wherein the two or more serotypes of *Streptococcus pneumoniae* are different from that of *Streptococcus pneumoniae* in the step (a).

4. The method according to claim 1, wherein the *Streptococcus pneumoniae* is selected from the group consisting of serotype 1, 2, 3, 4, 5, 6A, 6B, 7F, 8, 9N, 9V, 10A, 11A, 12F, 13, 14, 15B, 17F, 18C, 19A, 19F, 20, 22F, 23F and 33F.

5. The method according to claim 1, wherein the *Streptococcus pneumoniae* is inactivated *Streptococcus pneumoniae* or live attenuated *Streptococcus pneumoniae*.

6. The method according to claim 1, wherein the *Streptococcus pneumoniae* is bivalent or more multivalent, inactivated *Streptococcus pneumoniae* or live attenuated *Streptococcus pneumoniae*.

7. The method according to claim 6, wherein the inactivated *Streptococcus pneumoniae* is prepared by one or more methods selected from the group consisting of irradiation, heating and chemical treatment; or the live attenuated *Streptococcus pneumoniae* is prepared by one or more methods selected from the group consisting of irradiation, heating, chemical treatment and genetic engineering.

8. The method according to claim 1, wherein the step (d) is the step of removing an aggregated complex induced by cross-reactivity in case where the presence of cross-reactivity is confirmed in the step (c), followed by removing the aggregated complex by mixing the collected serum repeatedly with *Streptococcus pneumoniae*, the serotype of which is confirmed to induce cross-reactivity in the step (c).

9. The method according to claim 1, wherein the step (d) is the step of removing an aggregated complex induced by cross-reactivity in case where the presence of cross-reactivity is confirmed in the step (c), followed by removing the aggregated complex by mixing the collected serum repeatedly with *Streptococcus pneumoniae*, the serotype of which is confirmed to induce cross-reactivity in the step (c).

10. The method according to claim 1, wherein the method further comprises the step (d-2) of confirming whether or not the cross-reactivity is removed by conducting nephelometry after mixing the *Streptococcus pneumoniae* in the step (c) with an antiserum from which the aggregated complex has been removed in the step (d).

11. The method according to claim 10, wherein the antiserum is mixed repeatedly with the *Streptococcus pneumoniae*, the serotype of which is confirmed to induce cross-reactivity in the step (c), followed by removing the aggregated complex until the result of nephelometry satisfies any one or more of the following (i) and (ii):
 (i) less than the nephelometric result value of 1.0 ug/ml of *Streptococcus pneumoniae*, the serotype of which is confirmed to induce cross-reactivity in the step (c), and
 (ii) less than the average nephelometric result value of blank+(3 ×standard deviation).

12. An antiserum of *Streptococcus pneumoniae* prepared according to the method of claim 1.

* * * * *